(12) United States Patent
Gardner (10) Patent No.: US 7,563,227 B2
(45) Date of Patent: Jul. 21, 2009

(54) INSTRUMENT FOR DIRECT LARYNGOSCOPY WITH A RIGID BLADE AND FLEXIBLE FIBEROPTICS

(76) Inventor: Glenn P. Gardner, 3404 Heritage Oak Ct., Oak Brook, IL (US) 60523

( * ) Notice: Subject to any disclaimer, the term of this patent is extended or adjusted under 35 U.S.C. 154(b) by 436 days.

(21) Appl. No.: 11/179,751

(22) Filed: Jul. 12, 2005

(65) Prior Publication Data

US 2006/0247497 A1   Nov. 2, 2006

Related U.S. Application Data

(60) Provisional application No. 60/676,387, filed on Apr. 29, 2005.

(51) Int. Cl.
*A61B 1/267* (2006.01)
(52) U.S. Cl. .................. 600/194; 600/153; 600/185; 600/188; 600/190; 600/193; 600/196; 600/197
(58) Field of Classification Search .................. 600/153, 600/185, 188, 190, 193–194, 196–197
See application file for complete search history.

(56) References Cited

U.S. PATENT DOCUMENTS

| 4,337,761 | A |   | 7/1982  | Upsher  |          |
|-----------|---|---|---------|---------|----------|
| 5,183,031 | A | * | 2/1993  | Rossoff | 600/131  |
| 5,184,603 | A | * | 2/1993  | Stone   | 600/193  |
| 5,261,392 | A |   | 11/1993 | Wu      |          |
| 5,443,058 | A |   | 8/1995  | Ough    |          |
| 5,489,256 | A | * | 2/1996  | Adair   | 600/133  |
| 5,607,386 | A | * | 3/1997  | Flam    | 600/120  |
| 5,645,519 | A | * | 7/1997  | Lee et al. | 600/114 |
| 5,665,052 | A |   | 9/1997  | Bullard |          |
| 5,776,052 | A |   | 7/1998  | Callahan |         |
| 5,842,973 | A | * | 12/1998 | Bullard | 600/194  |
| 6,146,402 | A |   | 11/2000 | Munoz   |          |
| RE37,861  | E |   | 9/2002  | Schneider |        |
| 6,585,642 | B2| * | 7/2003  | Christopher | 600/156 |
| 6,878,106 | B1| * | 4/2005  | Herrmann | 600/104 |
| 2004/0039250 | A1 |  | 2/2004 | Tholfsen et al. | |
| 2004/0210114 | A1 | * | 10/2004 | Simon | 600/185 |

* cited by examiner

*Primary Examiner*—Linda C Dvorak
*Assistant Examiner*—Matthew J Kasztejna
(74) *Attorney, Agent, or Firm*—Daniel M. Gurfinkel; Husch Blackwell Sanders Welsh & Katz (57) ABSTRACT

A laryngoscope and flexible viewing device having means to carry an endotracheal tube into a patient and method of using the device are provided. The device allows a single user to view the interior of a patient's anatomy and change the view to better determine the path for intubation. The device can be used by a single individual to simultaneously open the pathway to a patient's trachea and then deliver an intubation device, such as an endotracheal tube, without the assistance of another person. The device provides several options for the practitioner to both visualize the patient's larynx and deliver an endotracheal tube into the trachea, especially in patients considered to have difficult anatomy to intubate. The viewing device in a preferred embodiment is a fiberoptic scope and the device includes a pivoting means to allow the viewing means to provide a more panoramic view of the patient's throat area.

2 Claims, 8 Drawing Sheets

INSTRUMENT FOR DIRECT LARYNGOSCOPY WITH A RIGID BLADE AND FLEXIBLE FIBEROPTICS

The present application claims the priority of U.S. Provisional Patent application No. 60/676,387, filed on Apr. 29, 2005, and incorporates that application herein as if set forth in its entirety.

FIELD OF THE INVENTION

The present invention concerns a medical instrument that allows for both direct laryngoscopy with a rigid blade and indirect flexible fiberoptics in the same instrument. More particularly the present invention concerns a laryngoscope having a rigid blade to retract oropharyngeal tissue and a flexible fiberoptic scope with guidewire systems, to permit examination of the larynx during laryngoscopy of a patient as well as a means to intubate a patient.

BACKGROUND OF THE INVENTION

The intubation of a patient in need of medical care is a frequent occurrence in operating theaters, emergency rooms and other medical situations. The insertion of a tube, through which life saving and sustaining oxygen may be provided, must be made through the natural defenses provided in the human body. Namely, an endo-tracheal tube must be fed through the mouth and throat, past the epiglottis, larynx and then into the trachea. The epiglottis is generally a flap of tissue that overlies the glottic opening into the larynx to prevent passage of food into the trachea during eating. In order to intubate a patient, the epligottis must be moved aside in order to provide visualization and access to the larynx and the trachea where intubation is made. It is generally agreed that laryngoscopy of many patients, with the state of prior art technology is at times difficult, concomitantly making intubation difficult. In addition, once visualization of the vocal cords is accomplished, actual passage of an endotracheal tube between the vocal cords with state of prior art may also be difficult.

There are a number of laryngeal devices presently available for use in intubating patients. In most cases these devices comprise a first means to displace the epiglottis and a separate means to insert an endotracheal tube past the epiglottis and into the trachea. In patients assessed and considered difficult to intubate, the doctor, or other medical personnel, typically requires assistance to intubate patients with difficult anatomy when using almost all of the devices of the prior art. An extra hand is needed to maintain the patient in an appropriate position, with mouth open, for the insertion of the blade to displace the epiglottis, while a second medical practitioner manipulates the mandible, tongue or larynx externally, or inserts an intubation device in the patient and pushes an endotracheal tube into the patient's trachea.

While the cooperation of medical personnel is generally available such that intubation is almost never denied, however, it is desirable to provide medical personnel with the tools that allow for excellent care of patients while permitting additional medical personnel, previously needed to assist in intubation, to attend to other tasks and/or patients.

SUMMARY OF THE INVENTION

In accordance with the present invention, a rigid laryngoscope and flexible-viewing device with intubation means as one instrument is provided. The device of the present invention comprises a handle operationally attached to a viewing member and a direct laryngoscope blade, the viewing device comprising a flexible fiberoptic scope and rigid extension housing. The flexible fiberoptic scope further has a means for providing a variable angle view of the interior of a patient's anatomy; the flexible fiberoptic scope is operationally attached to the viewing member and is carried within a rigid C-shaped housing channel along the length of and adjacent to the rigid laryngoscope blade. In one embodiment of the present invention, there are means to extend the tip of the flexible fiberoptic scope beyond the tip of the rigid blade. The extended or retracted position can be locked in place with an available clip or other means. The device further has a means to cause, when desired, the distal end of the flexible fiberoptic scope to pivot to any angle in a range from a linear position to a first pivoted position and back through the linear position to a second pivoted position opposite the first pivoted position. In this manner a panoramic view of the patient's oral anatomy is provided. In one embodiment the means to pivot the end of the flexible fiberoptic scope through its arc of movement includes a ratcheting means, which can also be provided with means to lock the flexible tip scope in a desired position.

The laryngoscope blade of the present invention comprises a rigid element for effecting the opening of a passageway for an intubation device, in a manner known in the art with the use of a typical laryngoscopic blade. Typical laryngoscopic blades may be available in a variety of shapes and sizes, including straight or curved and such as Miller or Macintosh designs. The device of the present invention further comprises a means to carry an intubation device adjacent to the flexible tube such that the user can on his own view the interior of the patient's anatomy, provide an open passageway and deliver an intubation device into the patient's trachea.

In one preferred embodiment of the laryngoscope and flexible-viewing device of the present invention the viewing device comprises a fiber optic cable and viewing element. Further, the viewing element of the device is a lens. Further, in another embodiment, the viewing device is a television-like monitor and the device of the present invention is operationally attached to the monitor such that one or more persons can view a patient, on a screen, when the device is used.

In one preferred embodiment of the device of the present invention, the handle and viewing device are rotationally attached together for storage and also to provide novel angles, between the handle and viewer, to assist in direct viewing of the patient's larynx upon the initial insertion of the instrument into the patient's oropharynx. In several embodiments of the device of the present invention, the viewing member comprises an extension tube attached to the rigid blade, in which a flexible tube member is maintained, and a lens or monitor connection defined at its proximal end, operationally connected to the flexible tube. The extension tube of the viewing member is provided with means for telescopically extending, and subsequently retracting the member, so as to assist the user in viewing the patient's anatomy through the lens and flexible tube, by permitting closer inspection within the patient's larynx. The extended or retracted position of the flexible tube can be secured with a clip or other available means.

In the present invention the intubation device is a rigid laryngoscope and the flexible tube includes means to carry a guidewire with which to assist the guidance of the intubation device within the patient's throat. In a preferred embodiment, the means to carry the guidewire includes a slit defined within the flexible tube within which the wire is positioned. In the preferred embodiment the preferred guidewire is of a type having a pivotal end piece, located at its proximal end, designed to pivot from a first position parallel to the guidewire to a second position perpendicular to the guidewire, much in the way that a cufflink is kept within a shirt sleeve. The slit in the flexible tube can be made in a number of ways without departing from the novel scope of the present invention and in a preferred embodiment has a diameter slightly larger than the cross-sectional diameter of the guidewire. In a preferred embodiment, in its initial position the guidewire is housed within a hollow channel, having a size greater than 3 times the guidewire diameter, along the length of the flexible fiberoptic scope. The fiberoptic scope, in this embodiment lays in a rigid C-shaped channel housing located under the rigid blade.

The present invention further includes a method of utilizing the above described device. The method includes insertion of the distal end of the device within the patient's mouth, utilizing the viewing means to provide better hand eye coordination in finding and displacing the epiglottis and subsequently visualizing their vocal cords. Lifting the epiglottis with the blade portion of the device, visualizing the vocal cords directly, or through the flexible fiberoptic scope, and then guiding an endo-tracheal tube into the patient's trachea directly. Alternatively, the endo-tracheal tube may be guided utilizing the guidewire systems held in the flexible tube member of one embodiment of the present invention. In addition, in one embodiment an umbilical-type detachable lasso cord is attached to the distal tip of the enclosed guidewire that is to be advanced into the trachea. The endotracheal tube is threaded over the lasso cord and then guided into the trachea. In this embodiment, the lasso cord is then detached from the guidewire, by operation of the device. The lasso cord of the present embodiment can also be provided with a pivotal proximal end piece, such as used in one embodiment of the guide wire (noted above).

A more detailed explanation of the invention is provided in the following description and claims and is illustrated in the accompanying drawings.

DETAILED DESCRIPTION OF THE ILLUSTRATIVE EMBODIMENT

While the present invention is susceptible of embodiment in various forms, there is shown in the drawings a number of presently preferred embodiments that are discussed in greater detail hereafter. It should be understood that the present disclosure is to be considered as an exemplification of the present invention, and is not intended to limit the invention to the specific embodiments illustrated. It should be further understood that the title of this section of this application ("Detailed Description of the Illustrative Embodiment") relates to a requirement of the United States Patent Office, and should not be found to limit the subject matter disclosed herein.

Figure 4A:
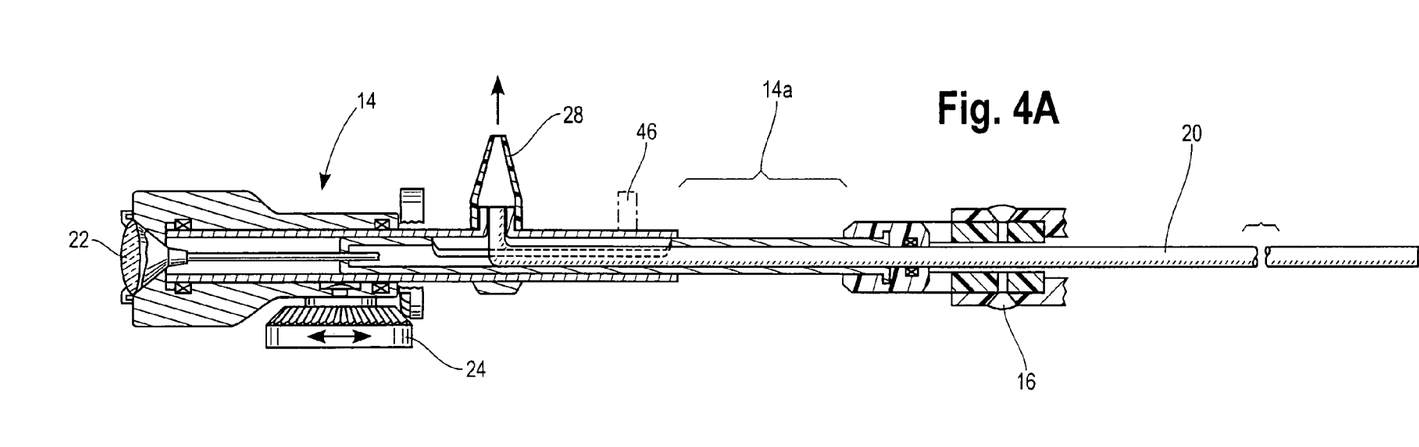
FIG. 4A is an elevational view, partially broken away, of the device of the present invention.
Figure 4B:
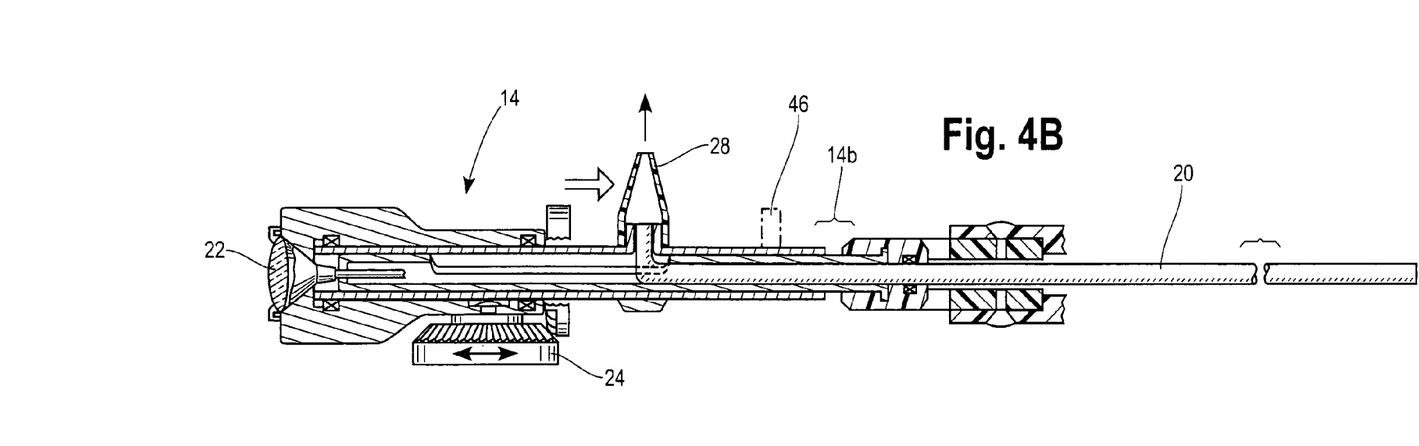
FIG. 4B is another elevational view, partially broken away, of the device of the present invention.
Figure 5:
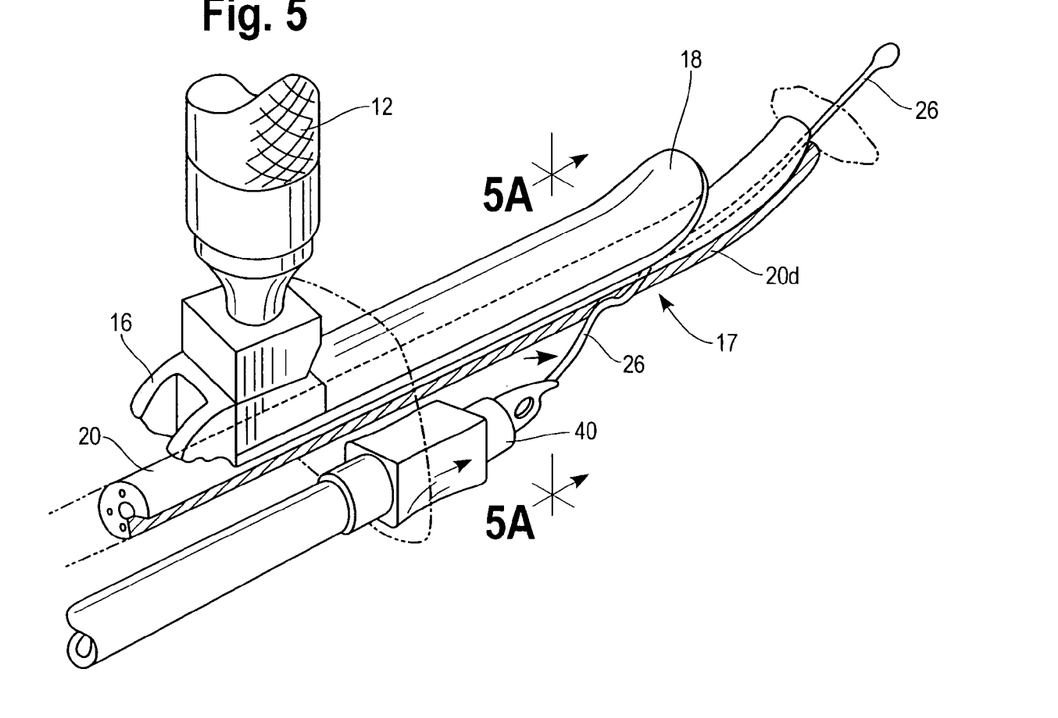
FIG. 5 is a perspective view, partially broken away, of the device of the present invention in a first position at the opening of the larynx with an endotracheal tube in a first carried position.
Figure 5A:
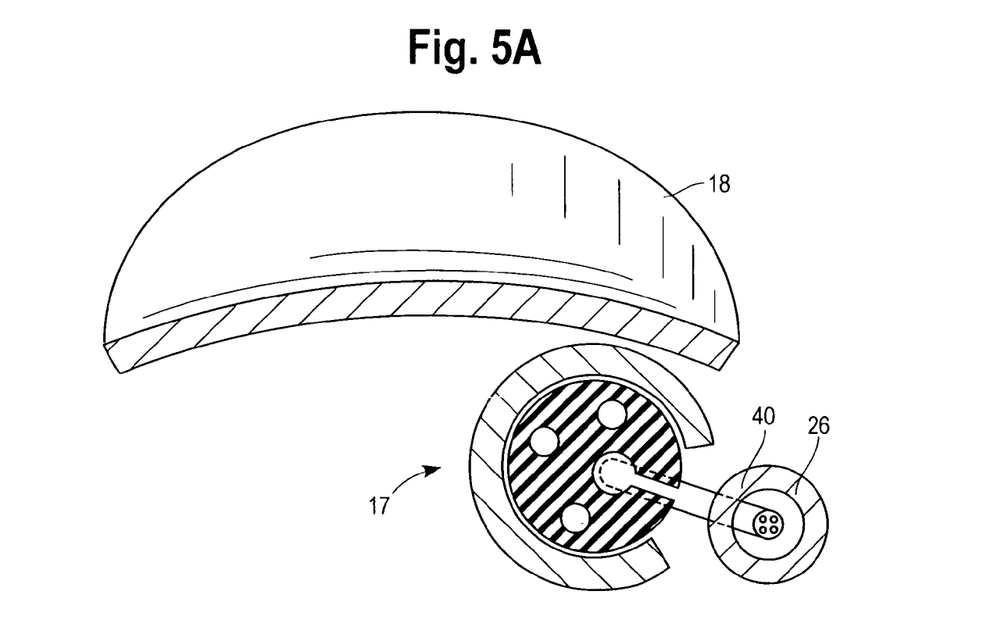
FIG. 5A is a partial cross sectional view and partial perspective view of the device of FIG. 5, taken along the plane of line 5A-5A and projected forward therefrom.
Figure 6:
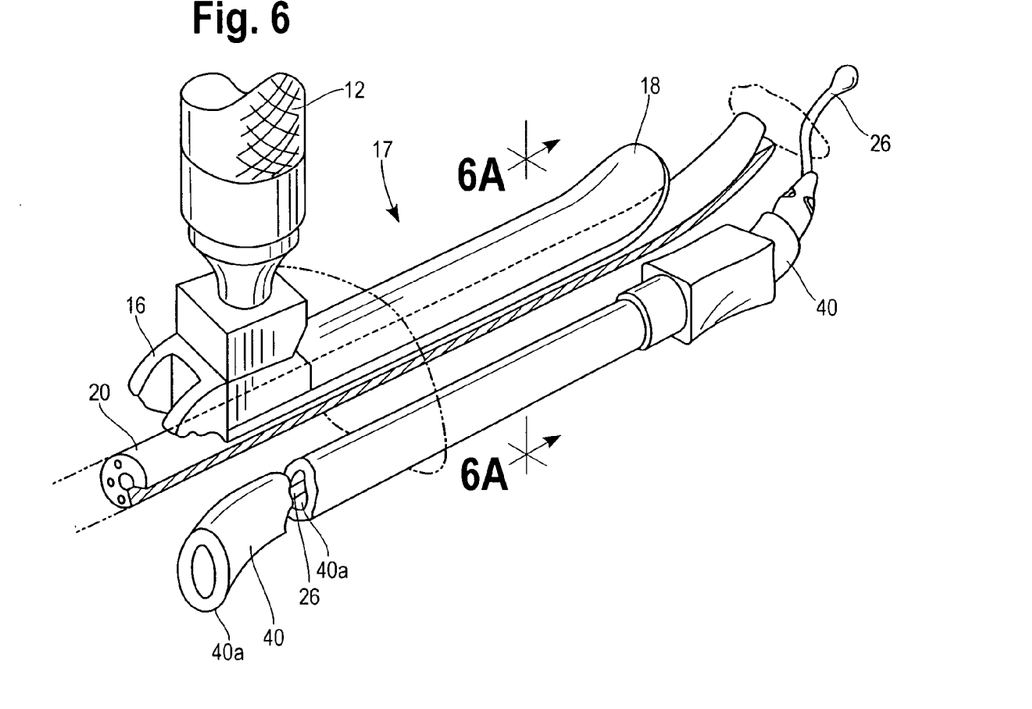
FIG. 6 is a perspective view, partially broken away, of the device of the present invention in a first position at the opening of the larynx with an endotracheal tube in place for intubation.
Figure 6A:
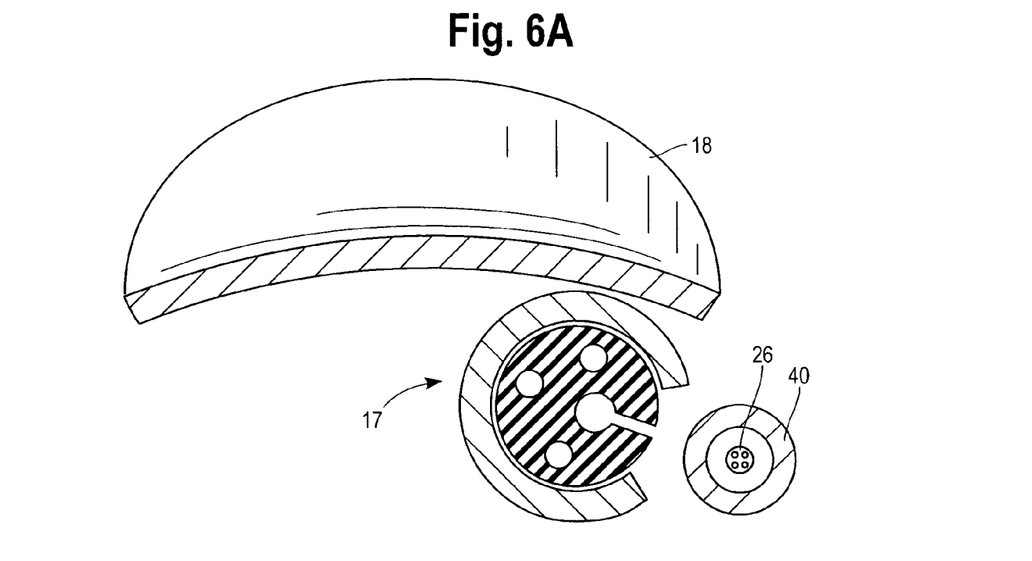
FIG. 6A is a partial cross sectional view and partial perspective view of the device of FIG. 6, taken along the plane of line 6A-6A and projected forward therefrom.

Referring to the figures, a laryngeal device or laryngoscope 10 having a handle 12 and a viewing member 14 is provided. Viewing member 14, in a preferred embodiment is made so that it can telescope between a first extended position 14a (FIG. 4A) and a second contracted position 14b (FIG. 4B). Telescoping portion 14, in the present embodiment, is attached at hinge 16 to a blade portion 17, including a blade 18. Telescoping portion 14 is also, in one embodiment, hingedly attached, near handle 12, such that telescoping portion 14 can be placed in a first folded position parallel to handle 12 when in a first stored position and during the initial insertion into the patient's mouth (see phantom lines). It will be understood that while the connection between the major components of the device of the present invention is shown as a hinged the elements, of the device, can be attached together in different manners, all well known to persons having ordinary skill in the art, without departing from the novel scope of the present invention. As noted above, viewing member 14, further, can be placed in a first contracted position or in extended position and can be placed in an infinite number of positions between the first extended position and the second contracted position, so that the user can place the device in an optimal viewing position. The uses for such telescopic action will be discussed in greater detail below.

Figure 1:
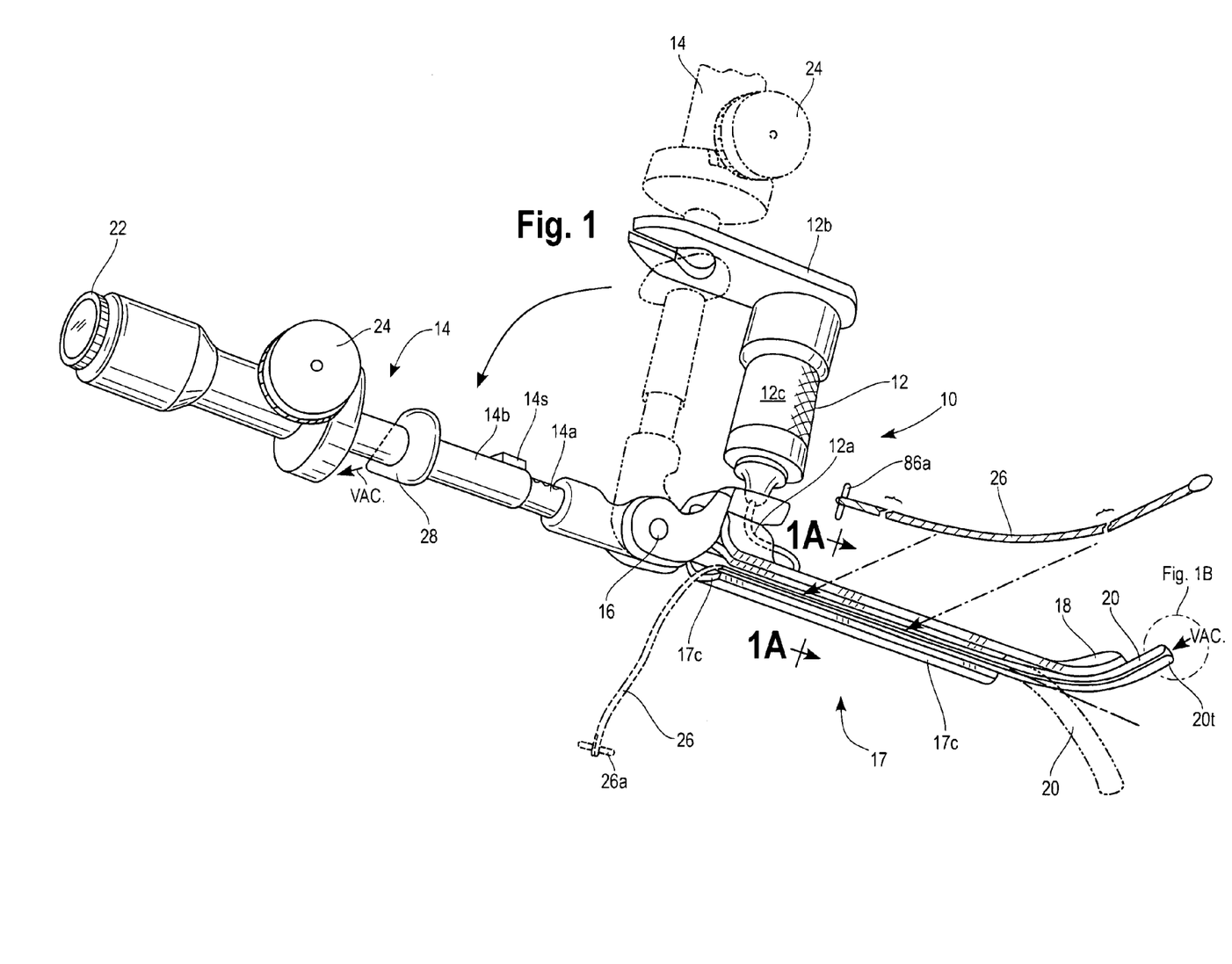
FIG. 1 is a perspective view of a device made in accordance with the teachings of the present invention.
Figure 1A:
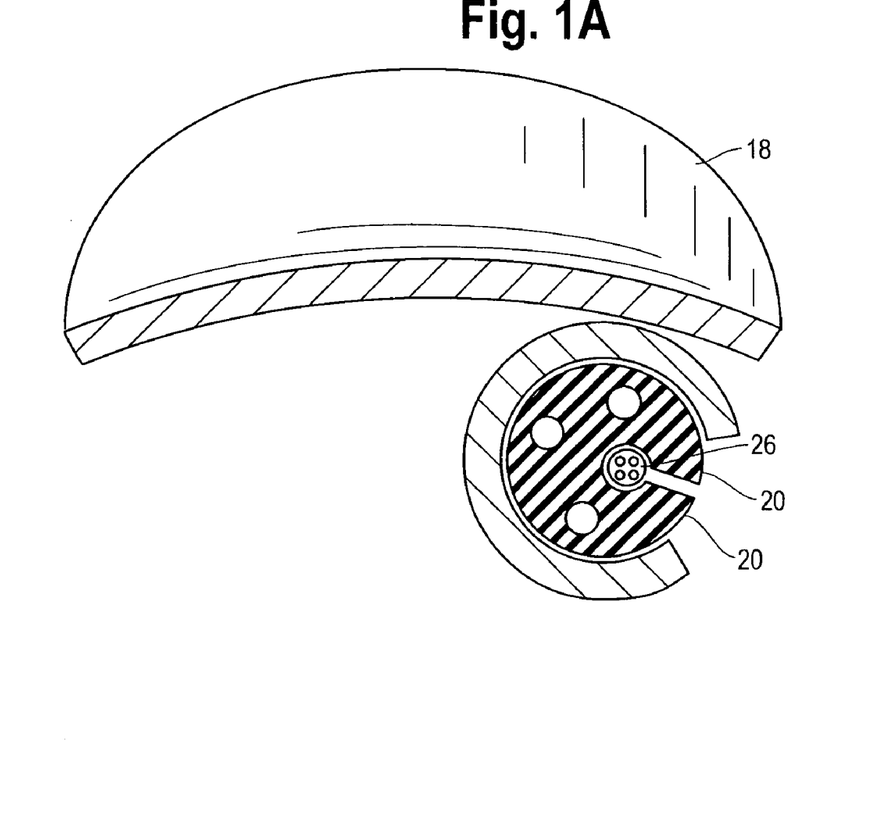
FIG. 1A is a cross-section of the device of FIG. 1, taken along the plane of line 1A-1A of FIG. 1.
Figure 1B:
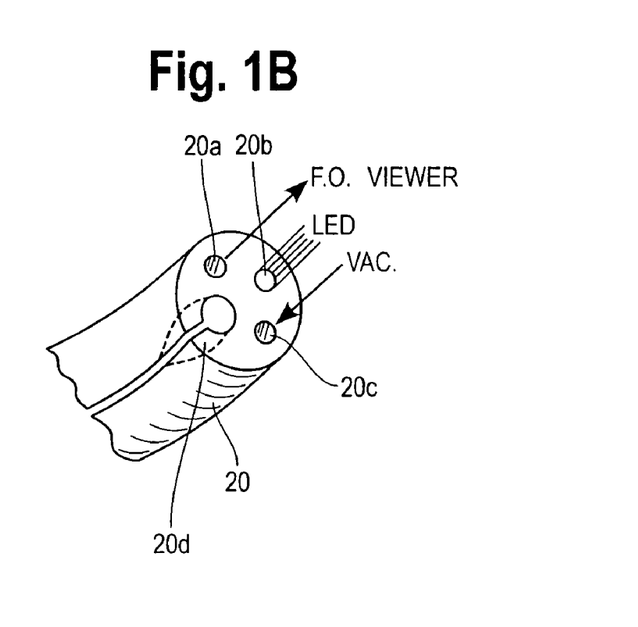
FIG. 1B is an exploded perspective view of element FIG. 1B of FIG. 1.
Figures 1C, 2A, 2B, 3A:
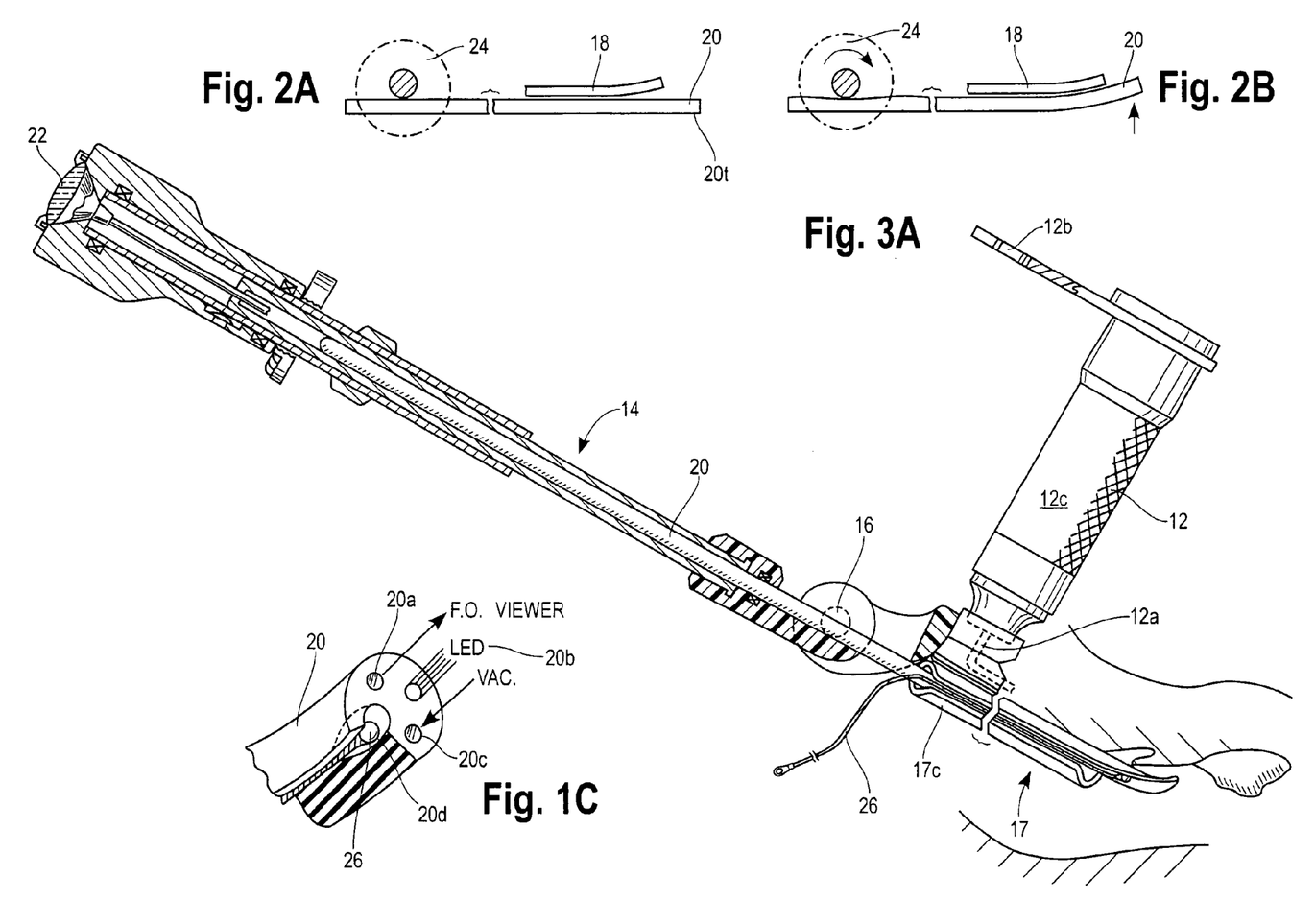
FIG. 1C is an partially cut-away exploded perspective view of element FIG. 1B of FIG. 1.
FIG. 2A is a schematic representation of one embodiment of the ratcheting mechanism of the device of FIG. 1.
FIG. 2B is a second schematic representation of one embodiment of the ratcheting mechanism of the device of FIG. 1.
FIG. 3A is an elevational view, partially broken away, of the laryngological device of the present invention in place in a patient's body, with a flexible tube in a first position.

Referring again to FIG. 1, it will be seen that the present invention of the device includes a flexible tubular member 20, adjacent to the blade portion 18, an eyepiece 22 and ratcheting member 24, both operationally attached to the flexible tubular member 20. Flexible tube member 20, in a preferred embodiment, can be made to advance forward so that tip 20t of member 20 is distal of the end of blade 18 within the rigid C-channel housing 17c along the underside of the blade, to provide a better view of the patient's anatomy. Tubular member 20, as shown in FIG. 1B can include a number of useful implements including an optical view member 20a, comprised in a preferred embodiment of a fiber optic scope; an illumination means 20b, which in a preferred embodiment comprises a second fiber optic cable attached, at a more proximal end to an illumination source such as an LED lamp; a suction entry point 20c, which in a preferred embodiment is attached to a vacuum port 28 (which in turn can be connected to a suctioning device external to the laryngoscope 10). Tubular member 20 further includes a transversal opening 20d defined generally along its entire length. Opening 20d is defined in member 20 so as to accommodate a guidewire 26. Opening 20d is generally a slit having a dimension slightly larger than that of the preferred guidewire 26 at its opening, with its full length channel being about 3 times the diameter of the guidewire, that will be carried therein, such that the guidewire 26 can be peeled out from tubular member 26 when desired, as explained in greater detail below. It will be understood by persons having ordinary skill in the art that the distal tip opening 20d will be larger than the diameter of channel 20d, so as to allow for the full and complete retraction of the distal tip of guidewire 26 into the distal tip of flexible tube 20, which is shown having a specialized shape and diameter.

In a preferred embodiment of the present invention, guidewire 26 includes a novel retention member 26a for use in association with the laryngoscope 10. Further, in one embodiment, a guidewire 26 having a distal tip holding member 26d is provided to assist in the carrying of a specialized cord so that intubation into the trachea below the vocal cords is facilitated, this will be explained in greater detail below. A more detailed explanation of the use of the guidewire 26 and the retention member 26a will be made below. It will be understood by persons having ordinary skill in the art that while a number of desirable elements of flexible member 20 are shown other elements can be substituted and some of those shown can be eliminated by persons having ordinary skill in the art, from flexible tube 20, as desired or desirable, without departing from the novel scope of the present invention.

Handle 12 of the laryngoscope 10 provides a location for grasping the device so that its use within a patient can be facilitated. Handle 12, in a preferred embodiment can house a power source (not shown) such as a battery that can provide power to an illumination means located at the distal end of the rigid blade 18 as in conventional laryngoscopes. In such a situation an LED lamp (not shown) can be housed in the handle 12 and a fiber optic cable 12a can deliver light from the LED lamp at the end of the rigid blade as is common in the field of the present invention. Handle 12 can in a preferred embodiment includes a holding means 12b, having means to grasp and hold viewing member 14. While a particular type of holding means 12b is shown, it will be understood by persons having ordinary skill in the art, that any means capable of holding viewing member 14 in its stored position can be utilized without departing from the novel scope of the present invention. It will be understood that other types and means to hold the device of the present invention, similar to or different from handle 12 can be used without departing from the novel scope of the present invention. In the illustrative embodiments, handle 12 is shown with a knurled surface to facilitate holding and manipulating the device of the present invention in typical wet environment in which the device is used. However, it will be understood by persons having ordinary skill in the art, that handle 12 can be configured differently, as needed, to facilitate its use in whatever environment the user is in, without departing from the novel scope of the present invention. In one embodiment of the handle 12 a power source, not shown, such as a battery and/or a rechargeable battery can be encased to provide power to a light source. In a further embodiment a separate light source entry point 46 (FIGS. 4A and 4B) is provided, a light element (not shown) can be attached to the entry point 46 to provide light via the viewing element's fiberoptics to the distal tip of 20b when positioned within the patient's larynx. As is known to persons having skill in the art any manner of light source can be attached thereto, such as a portable AC powered lamp source or a battery-held lamp source, without departing from the novel scope of the present invention.

Blade portion 17 is provided with a laryngeal blade 18 having a typical straight or curved size and shape, as conventionally known to the art, that permits the user to easily insert the device in a persons throat and move the glottis such that an endotracheal device (described below) can be inserted within the trachea. The use of a typical laryngoscope is well known to medical personnel. Blade portion 17 further includes means to hold the flexible tube portion 20, which includes, as shown in FIG. 1B, a fiber optic viewing device 20a, an LED light source 20b, a suction point 20c (attached to a vacuum means, as described in greater detail below) and a guidewire carrier means 20d. In a preferred embodiment of the present invention, a generally "C"-shaped rigid channel 17c is provided to act as a means to hold flexible tube 20 and to act as a loose guide for the flexible tube when it is advanced through the device. In a preferred embodiment of the present invention, channel 17c has a length approximately the length of blade 18 less approximately 2 cm proximally and 3 cm distally, to allow for ease of movement of the flexible member. It will be understood by persons having ordinary skill in the art that channel 17c can be made of different lengths and have a different cross-sectional shape without departing from the novel scope of the present invention.

Figure 3B:
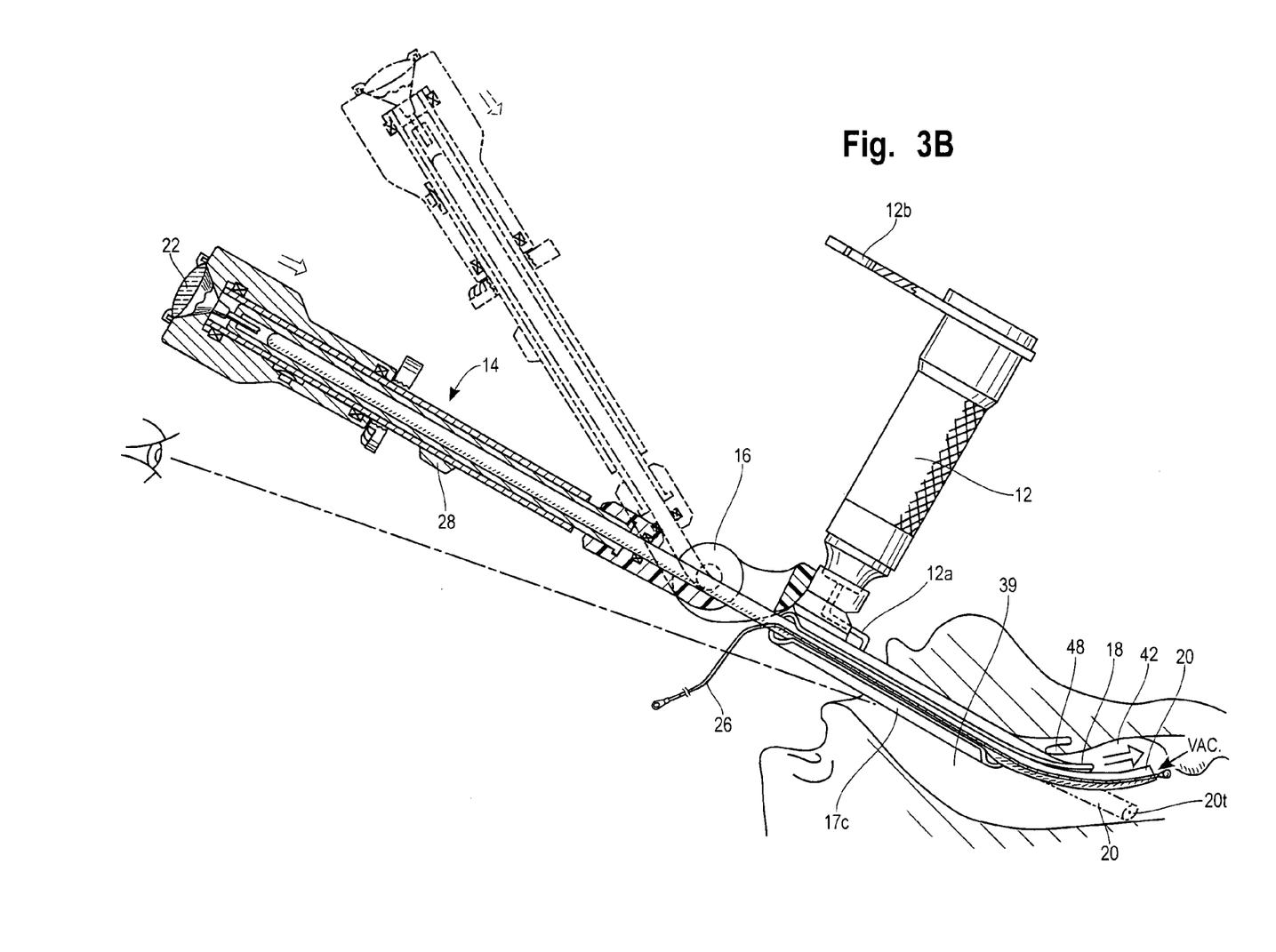
FIG. 3B is a second elevational view, partially broken away, of the device of FIG. 3A in place in a patient's body, with the flexible tube in an advanced position, showing possible movement in phantom.

The device 10 of the present invention includes means to peer into the throat from a viewer 22, such as a lens or, in one embodiment, a television monitor attached to the viewing means in a manner well known in the art. The device 10 further includes, in the illustrative embodiment, a ratcheting means 24 which when rotated causes the flexible tube 20 to pivot alternatively up from an axis 20x parallel to the axis of the device 10 and down from that axis 20x. In this manner the user can achieve a generally panoramic view of the interior of the patient's throat, so as to place (the blade 18 in the appropriate place so that) an endo-tracheal tube 40 (FIGS. 5-8) can be inserted into the trachea 42 (FIG. 3B). Further, as explained above and illustrated in FIGS. 3B, 4A and 4B viewing member 14 can be moved from a first contracted position (FIG. 4B) to an extended position (FIG. 4A), or any position there within, to the effect that flexible tube member 20 is, when viewing member 14 is moved to the extended position, is thrust forward, as shown in FIG. 3B. Movements within the viewing member 14, in a preferred embodiment, are produced by providing telescoping segments, inner segment 14a and outer segment 14b. It will be understood that outer segment 14b will slide over inner segment 14a permitting movement of flexible tube 20 which is operationally attached within inner segment 14a to outer segment 14b. The distal end of 14b will retain a locking mechanism 14s, such as a pin in hole system (see FIG. 1), where 14b carries a rigid pivoting pin, which will be placed within one of a series of holes located within the rigid wall of 14a when the distal tip of 20 has been satisfactorily positioned in the larynx. This or any other locking mechanism will prevent any unwanted extension or retraction of the viewing element while passing the guidewire or endotracheal tube during the use of the device of the present invention. When segment 14b is pushed forward inner segment 14a slides there within and flexible tube 20 is pushed forward, when it is desired to retract flexible tube 20, outer segment 14b is pulled back along inner segment 14a.

Referring again to FIG. 1, the guidewire 26 in a preferred embodiment is provided with a holding means 26a as noted above. It will be understood by persons having ordinary skill in the art that the main body of guidewire 26 can be made in any manner typically associated with medical guidewire technology without departing from the novel scope of the present invention. In the illustrative embodiments a twisted cable member is show, however, any method of making such guidewire and any type of guidewire found useful to the present invention can be used without departing from the novel scope of the present invention. The holding means 26a of the illustrated guidewire 26 is pivotal, along an axis of rotation adjacent its connection to the guidewire 26. In this manner, the long axis of holding means 26a can be brought parallel to the main axis of the guidewire, such that guidewire 26 can be slid through cannular openings in the manner of an ordinary wire. However, because of the pivoting feature, when the holding means is moved from a parallel configuration it provides a means to retain the endotracheal tube on the guidewire before positioning and to stop the complete insertion of the wire beyond the proximal end of the endotracheal tube. This is particularly useful in its use in the present invention, where the loss of a guidewire in a patient's throat would likely cause choking and possibly death. As the device of the present invention can be used by one person alone, the means to assure the safe maintenance of the guidewire within elements of the present device, provides added security to a single health care provider.

Slit 20d, as described above, permits the carrying of a guidewire into the patient's throat to assist in placement of the endotracheal tube 40, as described below. The slit 20d in flexible tube 20 can be created in any number of ways, including by cutting, pre-molding in place or extrusion means, without departing from the novel scope of the present invention. In a preferred embodiment the slit is provided of a size such that the diameter of the guidewire to be inserted therein is slightly smaller than the slit. While this will permit the easier removal of the guidewire, the properties of the flexible tube 20 will hold the guidewire 26 in place until an appropriate force, as described below, is applied to the guidewire during intubation. It will be understood by persons having skill in the art that the dimensions of the slit in flexible tube 20 can be varied, in manners which will cause an effective holding force, without departing from the novel scope of the present invention. In a preferred embodiment, the housing channel 20d (length of channel 20 within the mouth) should have a diameter approximately 3 times the size of the slit opening or of the guidewire diameter.

In the use of the device of the present invention, a user will place an intubation device, preferably an endotracheal tube 40 onto holding means in device 10, specifically in the area below blade portion 17. A guidewire 26 is placed partially within a flexible tube 20 in a channel 20d and its proximal end is threaded through the channel 40a of the endotracheal tube 40. Initially, medical personnel can insert the device merely by eyeing the general location of the anatomy with respect to the instrument, as shown in FIG. 3B, while the viewing element 14 is in its "stored" or up position, as is typically done with standard rigid blades in the art. The device 10 is then guided such that the blade 18 is placed adjacent the glottis 46 such that the blade 18 can hold the epiglottis 48 open allowing access to the trachea 42 for the guidewire 26, flexible tube 20 and endotracheal tube 40. Once placed in the appropriate location for proceeding with intubation, the user then checks the position of the blade element 17 and blade 18 inside the patient by activating a lighting means, such as light element 20b, and peering through viewing element 22 into the mouth of the patient. The device 10, in combination with endotracheal tube 40, is then extended or contracted as necessary (see FIGS. 4A and 4B). The user manipulates the viewing tube 20 using ratcheting means 24 such that the distal end of the viewing tube moves alternatively upward and downward from a line parallel to the central axis x of the device, so as to provide a panoramic view of the throat 3. At this point in the procedure, once the vocal cords are visualized, the user may place an endotracheal tube into the trachea without the use of a guidewire or the user may choose to use one of the guidewire systems of the device of the present invention as explained herein. In the use of a preferred guidewire system, the guidewire 26 is pushed distally into the larynx past the vocal cords and into the trachea while remaining partially within channel 20d. Then the endotracheal tube 40 is advanced, peeling the guidewire 26 out of its channel 20d; endotracheal tube 40 is then advanced into and down the trachea 42 to intubate the patient. The guidewire 26 is then removed from the trachea and endotracheal tube.

The proximal end 40a of the endotracheal tube 40 can then be attached to a source of oxygen and other gases as required for treatment. In a preferred embodiment, the guidewire 26 is provided with holding means 26a (FIG. 1) such that as the guidewire is advanced it is safely held within device 10 so that it cannot be lost in the patient's mouth or throat.

Figures 7, 7A:
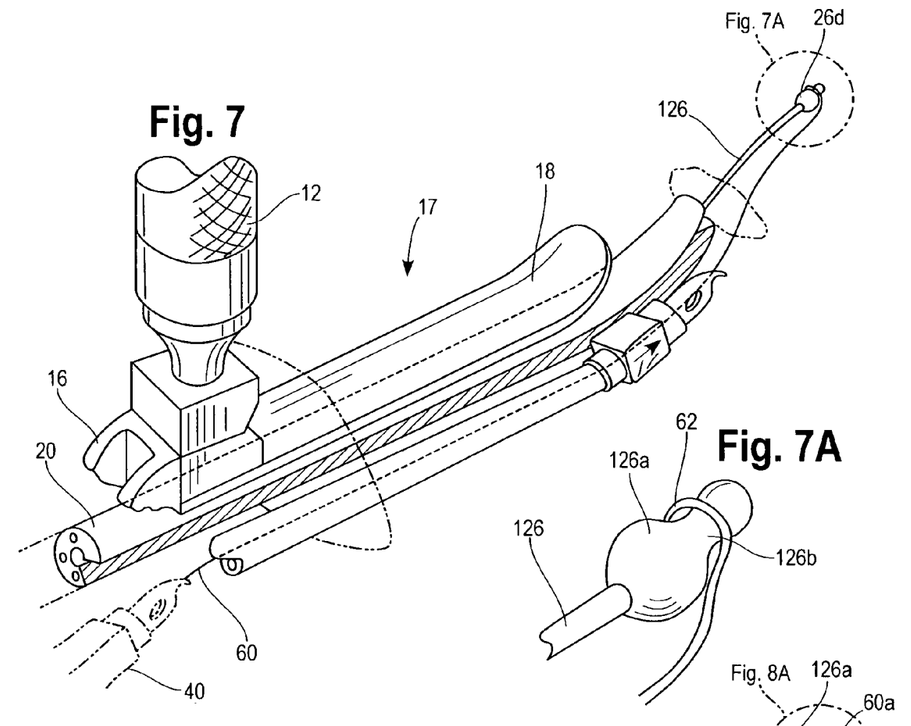
FIG. 7 is a perspective view, partially broken away, of another embodiment of the device of the present invention in a first position at the opening of the larynx with an endotracheal tube in a first carried position.
FIG. 7A is an exploded perspective view of element labeled "FIG. 7A" of FIG. 7.
Figures 8, 8A:
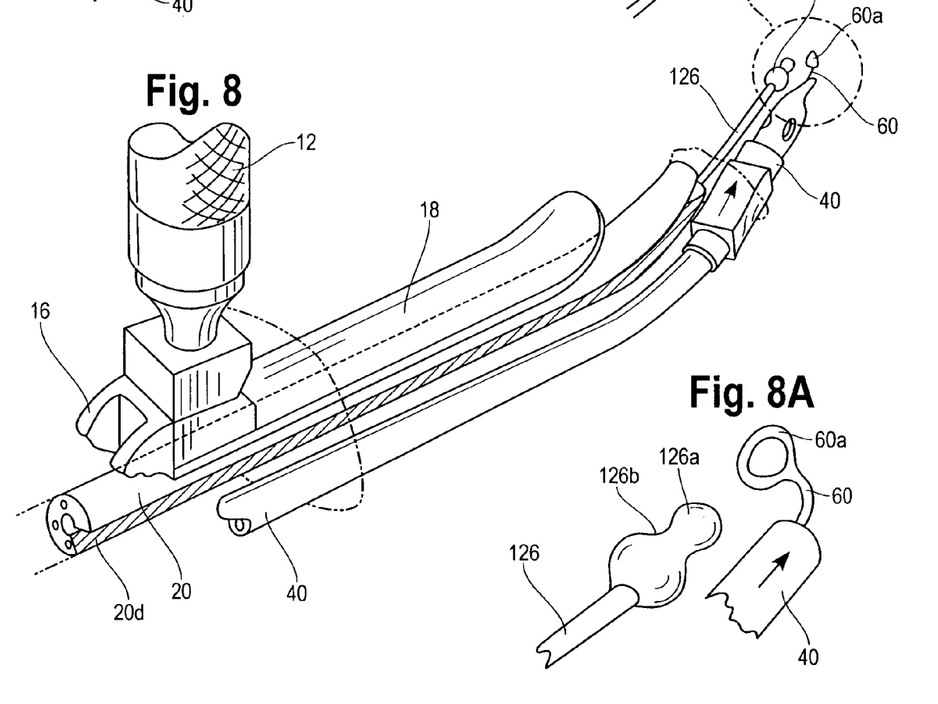
FIG. 8 is a perspective view, partially broken away, of the embodiment of FIG. 7 of the device of the present invention in a first position at the opening of the larynx with an endotracheal tube in place for intubation.
FIG. 8A is an exploded perspective view of element labeled "FIG. 8A" of FIG. 8.

In one embodiment of the device of the present invention, as shown in FIGS. 7 through 8A, a special umbilical tie 60, to assist in correctly placing the endotracheal tube 40, is shown. The umbilical tie 60 comprises a thin filament cord of a type well known in the art, having an elastic and/or detachable lasso element 62 comprising a means to grasp a guidewire 126. In the present embodiment, the device 10 and endotracheal tube 40 are assembled as noted above, with the exception that the umbilical tie 60 is fed into the endotracheal tube 40 such that its lasso end 62 emerges from the distal end to the endotracheal tube 40 and is attached to the guidewire 126. Guidewire 126 comprises a special head member 126a having a configuration similar to a bowling pin, such that first and second pseudo-spherical members are attached so that a "waist line" 126b is formed there between. Umbilical tie 60 is threaded within the endotracheal tube 40 such that lasso element 62 emerges from the distal end of endotracheal tube 40 and umbilical member 60 is extended so that the lasso element 62 loops over guidewire head 126a, resting within waist line 126b. The device 10 and endotracheal tube 40 so configured is then placed within the patient, in much the same manner as described above. However, tie 60 is now carried into the trachea by guidewire 126 while guidewire 126 remains in its channel 20d, along its length as described above, and the endotracheal tube is threaded over cord 60 below the vocal cords into the trachea. The user then releases cord 60 from guidewire 126, leaving the endotracheal tube in place. It will be understood by persons having skill in the art that tie 60 may be created in any manner known, including molding, braiding, extruding and others, without departing from the novel scope of the present invention. Further, while a lasso element is shown at the distal end of tie 60, it will be understood that other means for grasping and holding guidewire 26, including means molded or otherwise formed or more permanently attached to the distal end of the guidewire, can be used without departing from the novel scope of the present invention. In a preferred embodiment, lasso cord 60 is also provided with a holding element 26a on its proximal end, so as to hold and retain an endotracheal tube 40 over the cord 60 while in the procedure preparatory stage as well as to prevent loss of the cord 60 in the trachea after endotracheal intubation.

Although an illustrative embodiment of the invention has been shown and described, it is to be understood that various modifications and substitutions may be made by those skilled in the art without departing from the novel spirit and scope of the invention.

What is claimed is:

1. A laryngoscope and flexible viewing device with intubation means, comprising:
   a handle operationally attached to a viewing member and a laryngoscope blade;
   the viewing device comprising a flexible tube having a viewing device, the flexible tube further having means for providing a variable angle view of the interior of a patient's anatomy, the flexible tube being operationally attached to the viewing member and carried adjacent the laryngoscope blade, the flexible tube including a guidewire to guide the intubation device, the guidewire including an end piece pivotal from a first parallel to the guidewire position to a second perpendicular to the guidewire position to keep the guidewire attached to the laryngoscope and flexible viewing device;
   the device having means to cause, when desired, the distal end of the flexible tube to pivot to any angle in a range from a linear position to a first pivoted position and back through the linear position to a second pivoted position opposite the first pivoted position;
   the laryngoscope blade comprising a rigid element for effecting the opening of a passageway for an endotracheal tube; and
   means to carry an intubation device adjacent the flexible tube such that the user alone may view the interior of the patient's anatomy, provide an open passageway and deliver an intubation device.

2. A laryngoscope and flexible viewing device with intubation means, comprising:
   a handle operationally attached to a viewing member and a laryngoscope blade, the viewing member being rotationally attached such that it can be pivoted from a storage position to an operational position;
   the viewing device comprising a flexible tube having a fiberoptic cable and viewing lens operationally connected thereto, the flexible tube further having means for providing a variable angle view of the interior of a patient's anatomy, the flexible tube operationally attached to the viewing member and carried adjacent the laryngoscope blade, the flexible tube includes a guidewire to guide the intubation device the guidewire includes an end piece pivotal from a first parallel to the guidewire position to a second perpendicular to the guidewire position to keep the guidewire attached to the laryngoscope and flexible viewing device;
   the device having means to cause, when desired, the distal end of the flexible tube to pivot to any angle in a range from a linear position to a first pivoted position and back through the linear position to a second pivoted position opposite the first pivoted position;
   the laryngoscope blade comprising a rigid element for effecting the opening of a passageway for an intubation device; and
   means to carry an intubation device adjacent the flexible tube such that the user alone may view the interior of the patient's anatomy, provide an open passageway and deliver an intubation device.

\* \* \* \* \*